United States Patent [19]
Wilkes et al.

[11] Patent Number: 5,892,057
[45] Date of Patent: Apr. 6, 1999

[54] PREPARATION OF SULFO-N-HYDROXYSUCCINIMIDE SALTS

[75] Inventors: Marty Carey Wilkes, Rockton; Martin Lee Bremmer, Rockford, both of Ill.

[73] Assignee: Pierce Chemical Company, Rockford, Ill.

[21] Appl. No.: 932,851

[22] Filed: Sep. 18, 1997

[51] Int. Cl.$^6$ .................... C07D 207/416; C07D 207/10; C07D 307/36; C07D 307/06
[52] U.S. Cl. ................... 548/547; 548/548; 548/551; 549/262; 549/505
[58] Field of Search .................... 548/533, 534, 548/538, 547, 548, 551

[56] References Cited

U.S. PATENT DOCUMENTS

| | | | |
|---|---|---|---|
| 4,540,778 | 9/1985 | Tessler et al. | 536/114 |
| 5,536,643 | 6/1996 | Mock | 435/427 |

FOREIGN PATENT DOCUMENTS

| | | | | |
|---|---|---|---|---|
| 1-206253 | 3/1991 | Japan | | C07D 207/416 |

OTHER PUBLICATIONS

*Fiesor & Fiesor Organic Chemistry*, Listing of Chemical Compounds, 10 Pages, (Publication Date prior to the filing of this application).

"Aldrich Chemical Supply Handbook", 3 Pages, (Publication Date prior to the filing of this application).

"EZ–Link Biotinylation Reagents Reactive Toward Amines", *Biotinylating Reagents*, Pierce 1997 Product Catalog, 22 pages, (1997).

Akiyama, M., "Synthesis of N–Hydroxymaleimide and N–Hydroxyitaconimide and their Related Derivatives", *J.C.S. Perkin I.*, pp. 2122–2125, (Oct. 22, 1979).

Akiyama, M., et al., "A New Approach to the Polymer Reagent for Peptide Synthesis: Preparation of N–Hydroxysuccinimide Ester Polymers Via Polymerizable Active Esters", *Tetrahedron Letters*, No. 13, pp. 1015–1018, (1976).

Hess, R., et al., "Covalent Immunochemical membrane Labeling of Viable Cells with K698–T708, a Simian Virus 40 Tumor Antigen–Derived Peptide", *Peptide Research*, vol. 7, No. 3, pp. 146–152, (1994).

Kung, C.E., et al., "Interactions Between Sufactand Alkyl Sulfo–N–Succinimidyl Esters and Collagen Fibrils", *JALCA*, vol. 88, pp. 12–24, (1993).

Michich, T.J., et al., "Soap–Based Detergent Formulations. XVI. Surface Active Sulfosuccinimides", *Journal of The American Oil Chemists' Society*, vol. 52, pp. 451–454, (Nov. 1975).

Mikolajczyk, M., et al., "Recent Developments in the Carbodiimide Chemistry", *Tetrahedron Report R101*, vol. 37, pp. 233–284, (1981).

Narita, M., et al., "The Dehydration of N–Benzyloxy and N–Hydroxymaleamic Acid and the Isomerization of N–Benzyloxyisomaleimide", *Bulletin of the Chemical Society of Japan*, vol. 44, pp. 437–441, (1971).

Staros, J.V., "Membrane–Imperameant Cross–Linking Reagents: Probes of the Structure and Dynamics of Membrane Proteins", *Accounts of Chemical Research*, vol. 21 No. 12, pp. 435–441, (Dec. 1988).

Staros, J.V., "N–Hydroxysulfosuccinimide Active Esters: Bis(N–hydroxysulfosuccinimide) Esters of Two Dicarboxylic Acids Are Hydrophilic, Membrane–Imperameant, Protein Cross–Linkers", *Biochemistry*, vol. 21, pp. 3950–3955, (1982).

Wang, S.S., et al., "Enhancement of Peptide Coupling Reactions by 4–dimethylaminopyridine", *Int. J. Peptide Protein Res.*, vol. 18, pp. 459–467, (1981).

*Primary Examiner*—Johann Richter
*Assistant Examiner*—Dominic Keating
*Attorney, Agent, or Firm*—Schwegman, Lundberg, Woessner & Kluth, P.A.

[57] ABSTRACT

The salt of a sulfonated succinic acid is cyclized, then converted to novel sulfonated hydroxamic acids by reaction with hydroxylamine (which is added or formed in situ), and the novel hydroxamic acid is then cyclized to the sulfo-N-hydroxysuccinimide salt. This synthetic procedure is simple, direct, and more rapid than present procedures for synthesis of the succinimide. Novel sulfo-hydroxamic acid intermediates are formed during this procedure.

11 Claims, No Drawings

PREPARATION OF SULFO-N-HYDROXYSUCCINIMIDE SALTS

BACKGROUND OF THE INVENTION

1. Field of the Invention

The present invention relates to a method for the synthesis of sulfo-N-hydroxy succinimide salts, novel reduced-impurity or impurity-free salts, and novel intermediate hydroxamic acid sulfonate salts.

2. Background of the Art

Sulfo-N-hydroxy succinimides (often referred to as "Sulfo-NHS" or "S-NHS") including the acid and salt counterparts have a wide range of utility in a number of broad commercial areas, including but not limited to reagents for the manufacture of biotinylation reagents, oil well drilling agents, chemical and biological assay reagents, crosslinking agents for organic biological systems or polymer systems, side chain modifying agents, solubilizing agents, reactants, markers, and the like. The class may be generally represented by the formula below, representing the central nucleus:

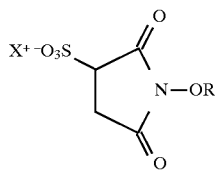

Wherein $X^+$ is a cation and R is H or an organic group, or especially any organic group formed from a compound R—OH wherein R—OH is an acid, and the symbolic extraction of OH (the hydroxyl) may leave the group R—, forming an ester with the remainder of the central nucleus. Examples of preferred R—OH compounds are acetic acid, LC-biotin suberic acid, biotin, suberic acid, 4-[N-maleimidomethyl]cyclohexane-1-carboxylic acid, and the like. The 2- and 3- positions on the central nucleus may also be substituted. The cation may be $H^+$, monovalent cations (such as $H^+$, $Na^+$, $Li^+$, $K^+$, $NH_4^+$, $Cs^+$, other inorganic cations, organic cations, etc.), or polyvalent cations (including divalent cations) in which the remaining charge is satisfied by other anions (e.g., halides, nitrates, sulfates, phosphates, etc.) or forms a bis- or tris- configuration with other sulfo-NHS anions. This class of compounds is relatively expensive, mainly because of the expensive synthetic procedures which must be taken to obtain the product. Existing synthetic procedures must not only use a large number of reagents and involve a large number of synthetic steps, but the procedures involve the use of large volumes of solvents and different solvents which must be stripped after various steps as well as at the end of the procedure. The process cost involved in recapturing and stripping of the solvents is quite significant, and with increasing environmental concerns, the requirements for avoiding release of solvents into the atmosphere have become more strict and therefore more costly.

A typical synthetic process for the synthesis of sulfo-N-hydroxysuccinimide salt is known to follow the following route:

Maleic anhydride:

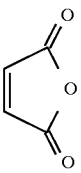

is reacted with furan:

to form a Diels-Alder reaction product:

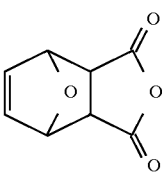

This intermediate product is extremely hazardous and special precautions are required in its handling. Workers must be protectively clothed and may even be required to wear full closure protective gear (e.g., full body suits), including self-contained helmets and at least filters if not self-contained air supplies. The crystals formed are hazardous to the eyes and are easily propelled and carried by air currents. Even removal of protective garments can be hazardous because of clinging crystalline product which can be put into the air by movement of the clothing. The Diels-Alder product is then reacted with hydroxylamine (e.g., hydroxylamine hydrochloride):

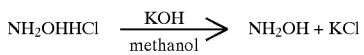

This step is done with potassium hydroxide and methanol (precipitating potassium as potassium chloride) producing an N-hydroxy succinimide adduct:

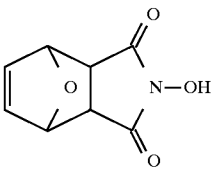

This product is usually washed in toluene and hexane. The N-hydroxy succinimide adduct is then reacted at the hydroxyl group. This reaction is performed by combining the adduct with phenylchloroformate

(which is a strong lachrymator) in various combinations of triethylamine, dichloromethane, toluene and hexane and sometimes dimethyl formamide to produce the next intermediate product:

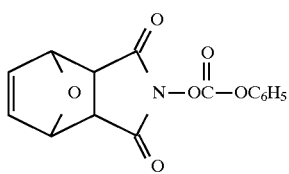

This intermediate product is in turn dissolved in a hydrocarbon solvent, e.g., a non-polar hydrocarbon solvent (e.g., decane) and heated to elevated temperature to form the next intermediate by removal of the protecting group.

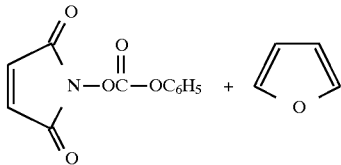

The temperature is elevated to about 170° C., which is above the flashpoint for decane (46° C.). The literature also shows the use of nitrobenzene as the solvent in this step. The reaction product tends to be a black, tarry product as result of using this commercially difficult step. t-Butyl catechol may be used as an antioxidant in this step.

This last intermediate is then reacted with sodium metabisulfite in ethanol to form the sodium salt of sulfo-N-hydroxysuccinimide, which is recrystallized from aqueous methanol, isopropanol, and washed with acetone:

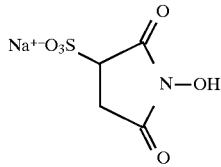

This product is produced in about 95–98% purity as an amorphous solid even after repeated purification, with clear evidence of the succinimide counterpart (the succinimide or hydrogen analog of the hydroxysuccinimide) being present in the final product:

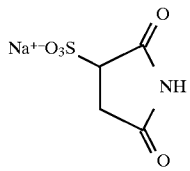

Overall yield of the process from the original maleic anhydride is about 25–28% theoretical, and the complete time of the process is about 50 days. Numerous solvent strips must occur, and a kilogram of product is usually produced in reaction vessels of fifty liters or more.

It therefore can be seen that the entire synthetic route is complex, has toxicity, environmental and hazard concerns throughout, is expensive, and is time consuming. Improved methods of synthesis are clearly desirable.

SUMMARY OF THE INVENTION

The salt of a sulfonated succinic acid is cyclized (e.g., with a Blanc reaction), then converted to novel sulfonated hydroxamic acids by reaction with hydroxylamine, and the novel hydroxamic acid is then cyclized (e.g., by dehydration) to the sulfo-N-hydroxysuccinimide salt. A process of forming a sulfo-N-hydroxysuccinimide by cyclizing a sulfohydroxamic acid is also described.

DETAILED DESCRIPTION OF THE INVENTION

The synthetic procedure of the present invention comprises fewer steps, can be performed in a batch process, requires fewer solvents, and produces novel intermediates and products without similar impurities as compared to processes of previous commercial use. Fewer hazardous materials are synthesized and used, and the process may be performed in a few days (e.g., 2–5 days) as compared to the approximate 50 days used for alternative procedures. Additionally, kilogram product amounts can be produced in a five liter batch process.

One process of the present invention may be described as a synthetic process comprising the steps of:
a) cyclizing a sulfo-succinic acid compound to form a monocyclic first product, and
b) opening the ring of said monocyclic first product in the presence of hydroxylamine (e.g., from an acid complex) to form a sulfo-hydroxamic acid.

The process may more specifically comprise cyclizing a sulfo-succinic acid having the central nucleus of:

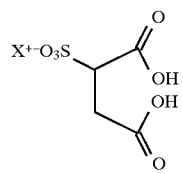

to form a monocyclic first product, and
b) opening the ring of said monocyclic first product in the presence of hydroxylamine acid complex to form a sulfo-hydroxamic acid. The process may be performed, for example, where the sulfo-hydroxamic acid comprises a compound having the central nucleus of:

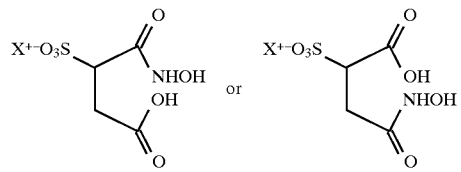

The process may then continue towards the sulfo-N-hydroxysuccinimide wherein the sulfo-hydroxamic acid is then cyclized, as by dehydration, to form a monocyclic sulfo-N-hydroxysuccinimide, wherein the sulfo-N-hydroxysuccinimide comprises the central nucleus of:

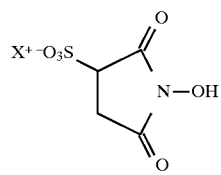

The cyclization (e.g., by dehydration) of the sulfo-hydroxamic acid is itself a novel process which may occur in the presence of methanol, water, acetic acid, acetic anhydride, dicyclohexylcarbodiimide and/or carbonyldiimidazole, as well as any other medium which assists or acts in the dehydration of the hydroxamic acid. The dehydration may be effected merely by leaving the hydroxamic acid in a solution of the additional material, as at room temperature in water, or at slightly elevated temperatures in water. This process may be done where opening a ring of said monocyclic first product in the presence of hydroxylamine acid complex to form a sulfo-hydroxamic acid is done in the presence of excess alcohol to produce a sulfohydroxamic acid ester (monoester or diester, depending upon the degree of excess) as a partial product. This ester subsequently performs in essentially the same manner as the acid in conversion to the sulfo-N-hydroxysuccinimide. The alcohol is preferably methanol, but any alcohol or even glycol may be used in this step, since the esterifying moiety is subsequently removed during cyclization or dehydration of the hydroxamic acid. Because of the relatively low number of steps and the reduced amount of residues, waste material and numbers of solvents, the alcohol or glycol is reformed during the dehydration, and this may be readily recovered. This further reduces costs by recycling the alcohol or glycol and avoiding its release into the environment.

The sulfo-N-hydroxysuccinimide, as elsewhere indicated herein, is present in the absence of the corresponding sulfosuccinimide (NH or hydrogen compounds) analogs. By further separation and control of enantiomeric components, the sulfo-N-hydroxysuccinimide may have proportions of R and S enantiomers of the sulfo-N-hydroxysuccinimide present, for example, as 100 to 55% or 100 to 50% (or more than 50%, e.g., 51% or more) R or S enantiomers, and may be present as a white, crystalline powder. The sulfo-N-hydroxysuccinimide in any of these forms may be present in the absence of sulfosuccinimide (hydrogen) analogs.

The process may begin with the appropriate sulfosuccinic acid, purchased commercially or formed by the sulfonation of succinic anhydride with sulfur trioxide. The first reagent is a compound having the basic core structure:

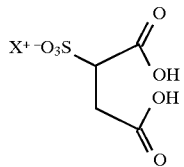

wherein $X^+$ is any cation, preferably a monovalent cation such as $H^+$, $Na^+$, $Li^+$, $K^+$, $NH_4^+$, etc. Where the term 'core structure' or 'groups' is used, the formula includes any substitution which does not change the actual atoms and bond structure shown. That is, for example with the succinimide and hydroxamic acid, on the unsubstituted portion between or intermediate the point of attachment of the sulfonate group and the carbonyl, any substitution may be present. The term 'having a core' or 'central nucleus' of Formula I therefore includes:

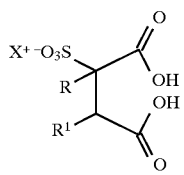

wherein R is H or any other desired substituent. For example, R may be alkyl, alkoxy, halo (I, Cl, Br, F), cyano, alkenyl, aryl (such as phenyl), etc. Likewise for $R^1$, $R^1$ may be hydrogen, alkyl, alkoxy, halo (I, Cl, Br, F), cyano, alkenyl, aryl (e.g., phenyl), etc. Where the terminology a 'compound of the formula' is used, that terminology excludes any substitution not specifically included in the description, e.g., allowing only the inherently understood $R^1$ at the position between the point of attachment of the sulfonate and the carboxy group. Likewise, the terminology of 'a core formula' or 'central nucleus' could prevent any substitution where a double bond was inserted into the backbone of the hydrocarbon chain of the compound.

The initial reagent having the core structure of the formula:

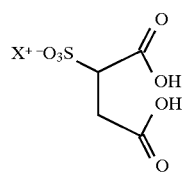

is cyclized. This cyclization reaction may be performed, for example, with the common Blanc reaction, in sodium hydroxide and acetic anhydride. The resulting first intermediate was a central nucleus of the formula:

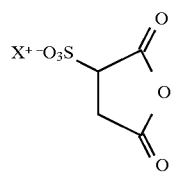

This is a known compound and has a CAS registry number. This first product is then subjected to a ring opening reaction with hydroxylamine (e.g., as an acid adduct, as with hydrochloride) in methanol, producing the novel hydroxamic acid salts:

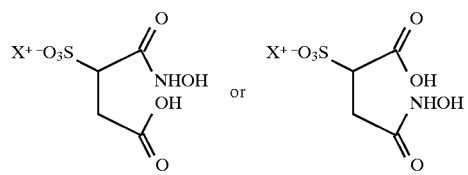

These are novel compounds which have not been reported in the literature. These compounds exist in many tautomeric and enantiomeric forms. The R and S enantiomeric position ("chiral center") exists at the point of attachment of the sulfonate group. The tautomeric forms include, for example:

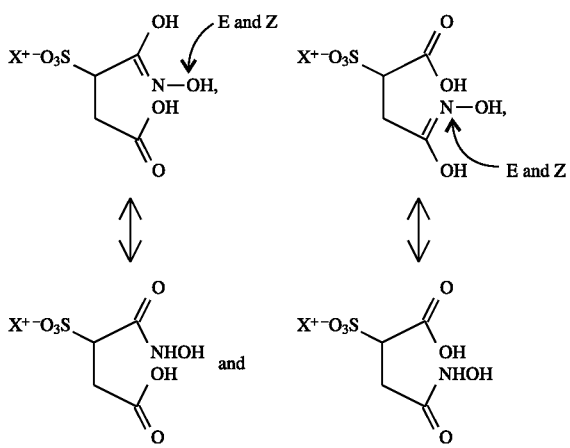

Enolization may also occur such as:

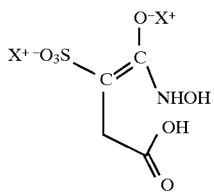

All of these structural variants in the structure of the sulfo-N-hydroxamic acid precursor compounds are of course expected to be statistically or potentially present as part of any composition containing the primary sulfo-NHS compound of interest, the presence of these variants being at least partially dependent upon the environment, pH conditions or other system influences on the composition.

At least three other distinguishing aspects of the present invention are noteworthy. These aspects may be individually or jointly present in the compositions of the invention. As previously noted, the process of the prior art used to produce sulfo-NHS produced the imide analog of the sulfo-NHS compound as a by-product, that succinimide (hydrogen analog) compound being represented by the formula:

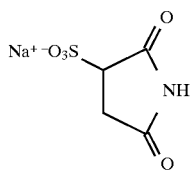

It is typically present in amounts greater than 1.0% by weight of the sulfo-NHS compound, even after repeated purification and the attempt to produce a pure sulfo-NHS composition in the process of the prior art. Even commercial sulfo-NHS contains this impurity, and of the 2–5% impurity in the commercial sulfo-NHS composition, this succinimide compound may be the largest contaminant. The process of the present invention produces a route to the sulfo-NHS compound and class of compounds which does not produce the succinimide contaminant. Therefore sulfo-NHS compositions which do not contain the succinimide counterpart are novel and, to date, have been produced only by means of the process described in the present invention. The sulfo-NHS compounds of the present invention may therefore be characterized as novel by the presence of less than 1% by weight of the succinimide counterpart, preferably less than 0.5% or less than 0.25%, and most preferably less than 0.1% down to 0% by weight of the succinimide.

Secondly, the resulting product from the process of the prior art which produces sulfo-NHS and the commercially available sulfo-NHS materials are amorphous solids. This is thought to be a result of the particular precipitation step used in the final step of the prior art process. The continuous batch process of the present invention produces distinct, white crystals. The clearly crystalline form of the sulfo-NHS compounds produced by this process is also distinct from the amorphous solid sulfo-NHS compounds produced by the prior art process.

Additionally, the sulfo-NHS compounds of the present invention may be separated into the separate enantiomers by a chiral separator. The R and S enantiomers may be separated into more highly purified isomers. This can be very important, as the R and S enantiomers will normally be used to make conjugates for use in assays, e.g., blotting or Elisa based immunoassays, etc. An unpurified mixture of enantiomers may provide a material with only 50% activity, especially if only one of the R and S enantiomers might be reactive towards a site. By providing a sulfo-NHS composition which may selectively contain higher proportions of R or S enantiomers, up to nearly 100% of either of the enantiomers, the resultant conjugates may be created to form enhanced functional systems. This can enable systems which are tailored for their degree of activity, without having to alter the remaining portions of the composition. For example, if an assay system were provided with a nominal activity of 10, using a 50/50 mixture of R and S enantiomers, the activity might be adjusted from 0 to 20 by appropriate selection of concentrations of the R or S enantiomer which was active in a particular assay. As previously mentioned, this chiral separation may be performed in a conventional manner (such as HPLC chromatography on a chiral column).

EXAMPLES

The following examples show the synthesis and then the use of the sulfosuccinic acid and sulfosuccinimide compounds of the present invention in the manufacture of chemically active species with known commercial utility. Many of the prepared compounds are commercially available by other synthetic routes, but would retain many of the impurities of the prior art synthetic procedures, such as the hydrogen counterpart of the N-hydroxy-succinimide discussed above.

Example 1

Preparation of Tetrahydro-2,5-dioxo-3-furansulfonic acid sodium salt

Tetrahydro-2,5-dioxo-3-furansulfonic acid sodium salt was prepared by stirring 1.71 moles of sulfosuccinic acid with 1.87 moles of sodium hydroxide at 50° C. until a milky suspension formed and then adding 1 kg acetic anhydride over 6 hours. After cooling, 1 L of ethyl acetate was added and the mixture was filtered. The filter cake was washed with 500 mL ethyl acetate. On drying 344.32 g of white crystalline product was obtained. $^{13}$C-NMR (d6-DMSO) 171.3, 167.2, 60.4, 34.0 ppm.

Example 2

Preparation of Sulfosuccinic monohydroxamic acid sodium salt

Sulfosuccinic monohydroxamic acid sodium salt was prepared by reacting tetrahydro-2,5-dioxo-3-furansulfonic acid sodium salt with hydroxylamine. 38.2 g hydroxylamine hydrochloride and 35.5 g potassium hydroxide were stirred at 5° C. in 300 mL methanol. A white precipitate formed and was filtered off.

The above methanol solution of hydroxylamine was slowly added to 90 g tetrahydro-2,5-dioxo-3-furansulfonic acid sodium salt in 100 mL methanol at 5° C. The mixture was stirred overnight and stripped to give 111.77 g white solid product. $^1$H-NMR (D$_2$O) 3.80–4.08 ppm m, 2.63–2.94 ppm m.

Example 3

Preparation of Sulfo-N-hydroxysuccinimide sodium salt

A suspension of 237.3 g sulfosuccinic monohydroxamic acid sodium salt in 700 g glacial acetic acid was slowly heated. At 70° C. TLC(thin layer chromatography, silica gel developed with 10% water/acetone) showed sulfo-N-hydroxysuccinimide sodium salt forming. A precipitate of sulfo-N-hydroxysuccinimide sodium salt formed at 80° C. after 2 hours which was cooled to room temperature and isolated by filtration to give 68 g sulfo-N-hydroxysuccinimide as a white solid. The filtrate was diluted with 1 L of acetone and the mixture was filtered again to recover an additional 70 g of sulfo-N-hydroxysuccinimide.

The combined product was purified by crystallization from 20% aqueous acetic acid. The product was dried under vacuum at 40–55° C. (98.4% by quantitative $^1$H-NMR in D$_2$O with maleic acid internal standard). The product contained less than 0.1% sulfo-succinimide impurity by C-18 ion pair HPLC.

Example 4

Preparation of 1-Hydroxy-2,5-dioxo-3-pyrrolidinesulfonic acid

1-Hydroxy-2,5-dioxo-3-pyrrolidinesulfonic acid was prepared as follows. 17 g of the sodium salt of sulfo-N-hydroxysuccinimide was dissolved in 50 mL water and applied to a preformed 50 g column of Ag1x8(OH—) anion exchange resin. The column was rinsed with 760 mL deionized water and the 1-hydroxy-2,5-dioxo-3-pyrrolidinesulfonic acid was eluted off with 200 mL 25% hydrochloric acid monitoring fractions by UV at 210 nm. The sulfo-N-hydroxysuccinimide containing fractions were stripped under high vacuum to produce 2.11 g viscous oil.

Example 5

Dicyclohexylcarbodiimide ring closure(dehydration) of Sulfosuccinic monohydroxamic acid sodium salt 2 g of sulfosuccinic monohydroxamic acid sodium salt in 150 mL dimethylformamide (DMF) was stirred with 1.75 g dicyclohexylcarbodiimide at 25° C. for 18 hours. The mixture turned an orange shade. The dicyclohexylurea precipitate was filtered off and the DMF solution was stripped under high vacuum. Ion pair HPLC showed sulfo-N-hydroxysuccinimide had formed.

Example 6

N,N-Carbonyldiimidazole ring closure of Sulfosuccinic monohydroxamic acid sodium salt 1 g of sulfosuccinic monohydroxamic acid sodium salt in 50 mL dimethylsulfoxide (DMSO) was stirred with 0.68 g N,N-carbonyldiimidazole. Carbon dioxide gas evolved over 30 minutes. The DMSO solution was stripped under high vacuum and 20 mL isopropanol was added. The white precipitate was filtered off and dried to give 0.3 g sulfo-N-hydroxysuccinimide as shown by $^1$H-NMR.

Example 7

Reaction of Sulfosuccinic monohydroxamic acid sodium salt with acetic anhydride

Sulfosuccinic monohydroxamic acid sodium salt prepared from 300 g tetrahydro-2,5-dioxo-3-furansulfonic acid sodium salt (as in Example 2) was treated with 650 mL acetic anhydride for 4 hours at 55° C. while distilling off water and acetic acid under vacuum. 1.5 L ethyl acetate was added and the white powder was filtered off and dried under a vacuum at 50° C. to give 305.53 g product. The product was mostly sulfo-N-acetoxy succinimide sodium salt by TLC comparison with an authentic standard and by NMR.

Example 8

Preparation of Sulfo-succinimide sodium salt 1.24 g maleimide, 1.22 g sodium metabisulfite and 30 mL water were stirred 30 min. UV spectra in water showed the formation of a peak at 197 nm. The solution was stripped to give 1.99 g white crystals. Ion pair HPLC gives a single peak at 5.57 min. (sulfo-N-hydroxysuccinimide 6.17 min.)

Example 9

Preparation of Sulfo-N-hydroxysuccinimide sodium salt via hydrolysis of sulfo-N-acetoxy succinimide sodium salt 30 g Sulfo-N-acetoxy succinimide sodium salt was dissolved in 200 mL acetic acid and 0.8 mL water. The mixture was heated to reflux for 30 min., cooled and 200 mL ethyl acetate was added. The white crystals were filtered off and dried under a vacuum to give 26.45 g product which was mostly sulfo-N-hydroxysuccinimide by $^1$H-NMR.

Example 10

Preparation of 3-methyl-2-sulfosuccinic acid sodium salt (cis and trans diastereomers)

3-Methyl-2-sulfosuccinic acid sodium salt was prepared as follows. 20 g Methylsuccinic anhydride was dissolved in 40 g 1,2-dichloroethane. 15.4 g solid sulfur trioxide was melted and added in portions to 140 g 1,2-dichloroethane in an addition funnel. The sulfur trioxide solution was added slowly to the anhydride solution and stirred overnight. 50 mL water was then added, followed by 7 g sodium hydroxide dissolved in 50 mL water. The layers were separated and the 1,2-dichloroethane layer was again extracted with 50 mL water. The combined water layers were stripped to give 42.2 g yellowish solid. $^1$H-NMR (D$_2$O) 2.65–2.80 ppm m, 2.47–2.58 ppm m, 1.04 ppm d J=7.07 Hz.

Example 11

Preparation of Tetrahydro-2,5-dioxo-4-methyl-3-furansulfonic acid sodium salt (cis and trans diastereomers)

40 g 3-methyl-2-sulfosuccinic acid sodium salt (cis and trans diastereomers) was stirred with 50 g acetic anhydride and then heated to 86 degrees Centigrade while distilling over acetic acid for 1.5 hours. 100 mL ethyl acetate was added and the mixture was filtered. The precipitate was washed with 100 mL ethyl acetate. The precipitate was dried to produce 16.0 g yellowish-white solid. $^1$H-NMR (d6-DMSO) 3.40 ppm d J=10.52 Hz, 2.92–2.98 ppm m, 1.28–1.31 ppm m J=7.12 Hz.

Example 12

Preparation of 3-methyl-2-sulfo-N-hydroxysuccinimide sodium salt (cis and trans diastereomers)

To 2.86 g potassium hydroxide in 50 mL of methanol cooled to 5 degrees Centigrade was added 3.53 g hydroxylamine hydrochloride. A white precipitate was filtered off.

To 10 g of tetrahydro-2,5-dioxo-4-methyl-3-furansulfonic acid sodium salt (cis and trans diastereomers) and 50 mL methanol at 5 degrees Centigrade was added the above hydroxylamine solution. The mixture was stirred overnight, allowing the mixture to warm to room temperature. The suspension was stripped to give 10.97 g product. TLC (Thin layer chromotography) using 10% water/acetone on silica gel gives a 0.05 r.f. spot reacting with potassium permanganate (turning yellowish white). The crude product was recrystallized from 100 mL warm acetic acid to give 9.27 g white crystals after washing with 150 mL ethyl acetate. $^1$H-NMR (D$_2$O)-4.02 ppm d, 3.88 ppm d, 3.00–3.14 ppm m, 1.35 ppm (cis) d J=7.5 Hz, 1.19 ppm (trans) d J=7.0 Hz. The ratio of trans to cis diastereomers was 60:40 by proton NMR integration.

The derivatives of the sulfo-N-Hydroxysuccinimides used in the art, when made from the sulfosuccinimide-free analogs (free of the hydrogen analogs) are distinguishable from the otherwise chemically identical derivatives by the absence of the analogs. The esterification derivatives, e.g.,

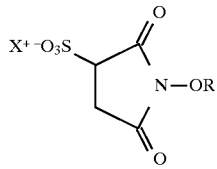

Wherein X$^+$ is a cation and R is H or an organic group, or especially any organic group formed from a compound R—OH wherein R—OH is an acid, and the symbolic extraction of the hydroxyl forms an ester group with the residue (less —OR) of the central nucleus. Examples of preferred R—OH compounds are acetic acid, LC-biotin suberic acid, biotin, suberic acid, 4-[N-maleimidomethyl]-cyclohexane-1-carboxylic acid, and the like, are also free of the hydrogen analog (the sulfosuccinimide as opposed to the sulfo-N-hydroxy succinimide) while the prior art ester derivatives would have some of that contaminant present. Therefore, the ester derivatives which are free of the sulfo-succinimide analog are also novel compositions.

What we claim is:

1. A sulfo-N-hydroxysuccinimide having a monocyclic central nucleus of the formula:

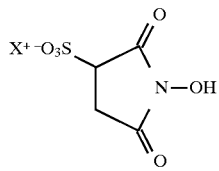

wherein X is a cation and which sulfo-N-hydroxysuccinimide is present as a white, crystalline powder.

2. The sulfo-N-hydroxysuccinimide of claim 1 which is present in the absence of sulfosuccinimide analogs.

3. The sulfo-N-hydroxysuccinimide of claim 1 in which the proportions of R and S enantiomers of the sulfo-N-hydroxysuccinimide are present as 100% to 50% R or S enantiomers.

4. The sulfo-N-hydroxysuccinimide of claim 2 in which the proportions of R and S enantiomers of the sulfo-N-hydroxysuccinimide are present as 100% to 55% R or S enantiomers.

5. A succinimide having the central nucleus:

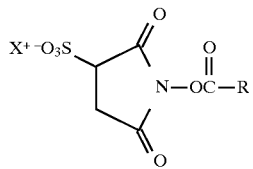

wherein X$^+$ is a cation and R is H or an organic group, wherein said succinimide is present as a white crystalline powder.

6. The succinimide of claim 5 wherein R represents a group such that R—COOH is an acid wherein esterification of the acid leaves the group RCOO—.

7. The succinimide of claim 5 wherein R— is any organic group formed from a compound R—COOH wherein R—COOH is an organic acid, and the esterification of RCOOH leaves the group RCOO$^-$ as an ester with the succinimide.

8. The sulfo-N-hydroxysuccinimide of claim 1 comprising less than 0.5% by weight of sulfosuccinimide analogs.

9. The succinimide of claim 5 wherein a compound ROH is an acetic acid, biotin, LC-biotin, suberic acid, or 4-cyclohexane-1-carboxylic acid, with R as defined above.

10. A white crystalline powder ester derivative formed through the esterification of the hydroxy group of the sulfo-N-hydroxysuccinimide of claim 1 said ester derivative having the general formula:

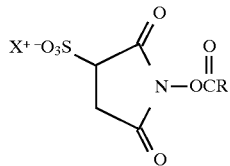

wherein X$^+$ is a cation and R is H or an organic group.

11. The ester derivative of claim 10 wherein said organic group is formed from a compound R—COOH wherein R—COOH is an acid, and the esterification leaves the group RCOO— to form an ester with the succinimide.

* * * * *